United States Patent [19]
Merrick

[11] Patent Number: 4,763,649
[45] Date of Patent: Aug. 16, 1988

[54] TECHNIQUE FOR CREATING A ZERO REFERENCE FOR AN EXTERNAL PRESSURE TRANSDUCER

[75] Inventor: Edwin B. Merrick, Stow, Mass.

[73] Assignee: Hewlett-Packard Company, Palo Alto, Calif.

[21] Appl. No.: 48,485

[22] Filed: Apr. 27, 1987

Related U.S. Application Data

[63] Continuation of Ser. No. 802,502, Nov. 27, 1985, abandoned.

[51] Int. Cl.⁴ .............................................. A61B 5/02
[52] U.S. Cl. .................................. 128/673; 128/692
[58] Field of Search ............... 128/672, 673, 675, 748, 128/687, 691, 692

[56] References Cited

U.S. PATENT DOCUMENTS

| | | | |
|---|---|---|---|
| 3,710,781 | 1/1973 | Huthcins et al. | 128/675 |
| 3,996,926 | 12/1976 | Birnbaum | 128/673 |
| 4,023,563 | 5/1977 | Reynolds et al. | 128/672 |
| 4,203,451 | 5/1980 | Panico | 128/672 |
| 4,232,373 | 11/1980 | Jackson et al. | 128/672 |
| 4,245,648 | 1/1981 | Trimmer et al. | 128/672 |
| 4,423,738 | 1/1984 | Newgard | 128/672 |
| 4,431,009 | 2/1984 | Marino et al. | 128/674 |
| 4,456,013 | 1/1984 | De Rossi et al. | 128/675 |
| 4,475,556 | 10/1984 | Reiff | 128/673 |

OTHER PUBLICATIONS

"Arterial Pressure Waveform Recording: A Clinical System", Wilkins et al., Bio-Med. Eng. 1972.

*Primary Examiner*—Max Hindenburg
*Attorney, Agent, or Firm*—Donald N. Timbie

[57] ABSTRACT

Apparatus for measuring the blood pressure of a patient, comprising a catheter, a first transducer mounted in an end portion of said catheter so as to produce at an output thereof a signal corresponding to blood pressure variation thereat, means defining an opening in said catheter at a point near said first transducer so that the blood pressure at said opening is the same as the blood pressure applied to said first transducer, means coupled to said first transducer for deriving a first signal in which the low frequency components of the signal provided by said first transducer are de-emphasized, and means including a second transducer coupled to said catheter at a point remote from said opening for deriving a second signal in which the high frequency components of the blood pressure variations at said opening are de-emphasized.

8 Claims, 1 Drawing Sheet

TECHNIQUE FOR CREATING A ZERO REFERENCE FOR AN EXTERNAL PRESSURE TRANSDUCER

CROSS REFERENCE TO RELATED APPLICATION

This application is a continuation of application Ser. No. 802,502, filed Nov. 27, 1985, now abandoned.

BACKGROUND OF THE INVENTION

The most accurate way of measuring the blood pressure in the heart or other internal organ of a patient is to insert a catheter having a transducer at its distal end through a blood vessel to the point of interest, but this increases the risk of blood clots and may abrade tissue near the heart. Current practice avoids these problems by coupling blood pressure at a peripheral site, such as in the wrist, to a transducer outside of the patient's body with a saline-filled lumen in a catheter. In the illustration of this technique shown in FIG. 1, an external transducer T is shown having a hollow pressure dome D, that is mounted pressure in the dome D is applied to a sensitive surface 2 that translates the pressure into a corresponding signal on output leads $L_1$ and $L_2$. Excitation is applied to the transducer T via leads $L_3$ and $L_4$. A tube 4 that communicates with the interior of the dome D is connected via a valve $V_1$ to a tube 6. Another tube 8 that communicates with the dome D is connected via a valve $V_2$ to a lumen in a catheter C, and the distal end of the catheter C is inserted into a blood vessel in the arm A of a patient P.

In use, the tubes 4, 6 and 8, the valves $V_1$ and $V_2$, the catheter C and the dome D are filled with a saline solution having nearly the same density as blood, and the catheter C is inserted into a blood vessel in the arm A of a patient P, e.g., in his wrist. The open end of the tube 6 is placed on a reference level indicated by the dashed line R that passes through the point at which the pressure is desired in the organ O. The valve $V_2$ is closed and the valve $V_1$ is opened. The signal on the leads $L_1$ and $L_2$ under this condition includes a first component due to the height of solution in the tube 6, in the tube 4 and in the valve $V_1$ above the sensing surface 2 and a second component called "transducer offset" that may add to or subtract from the first that is different for each transducer. The monitor or other device to which the leads $L_1$ and $L_2$ are coupled is then adjusted to a reading of zero pressure. Note that an opening B in the body of the transducer T permits atmospheric pressure to reach the underside of the sensing surface 2 so as to balance the effect of atmospheric pressure at the open end of the tube 6. Instead of manually adjusting the monitor to zero, the signal on $L_1$ and $L_2$ may be stored in a memory for numerical subtraction. Then the valve $V_1$ is closed and the valve $V_2$ opened so that the blood pressure of the patient at the organ O may be measured. A change in the height of the point in the arm A where the distal end of the catheter C is located has no effect on the pressure indicated by the transducer T.

A severe difficulty with such apparatus is that the compliance of the walls of the catheter C and the transducer T, as well as the inertia of the saline solution, impairs the frequency response so that the fidelity of the signal on the leads $L_1$ and $L_2$ is significantly less than optimum.

In order to improve accuracy, it has been proposed that the transducer be placed in a blood vessel in the body at a site remote from the organ generating the pressure of interest. However, a new problem arises. Consider the case of a catheter inserted into the radial artery in the wrist of a human patient for the purpose of indicating the pressure in the aorta. In this situation, the transducer is advanced only a few inches beyond the patient's wrist toward the heart. If the patient elevates his arm such that the transducer is raised by 13.8 mm, the associated instrumentation will indicate a pressure decrease of 1 mm Hg. If one assumes that a patient has the ability to vary his wrist elevation by ±1.0 meter, then a pressure measurement error of ±72 mm Hg can result. One obvious solution to this problem is to strap the patient's wrist to his body at the level of the organ so as to prevent the patient from moving his arm. Even this extreme measure has its limitations since patients may roll or be rolled from side to side to prevent fluid pooling in the lungs and for other reasons. This orientation change would also change the elevation relationship between the organ and the transducer site and introduce an error.

BRIEF DESCRIPTION OF THE INVENTION

In accordance with this invention, means including a catheter are provided for inserting an internal transducer into a blood vessel of a limb of a patient, e.g., in the wrist, and an external transducer is coupled via a lumen to the same point as the internal transducer. Because the mean value of the signals provided by the internal transducer are significantly affected by a variation in its elevation with respect to the point at which the blood pressure is desired, means are provided for de-emphasizing the low frequency components in its output signal that correspond to mean pressure. With known techniques, the signal provided by the external transducer can be made to have a mean value corresponding to the mean pressure at the point where the blood pressure is desired, but the high frequency components due to changes in pressure at the desired point are, because of tubing, compliance and fluid inertia, highly inaccurate. Accordingly, means are provided for de-emphasizing the high frequency components of signals that would otherwise be provided by the external transducer. An output signal that is unaffected by changes in elevation of the internal transducer and which faithfully corresponds to the blood pressure at the desired point in the body is provided by adding the signals derived from the transducers after the low frequencies of one and the high frequencies of the other have been de-emphasized.

DETAILED DESCRIPTION OF THE INVENTION

Figure 1:
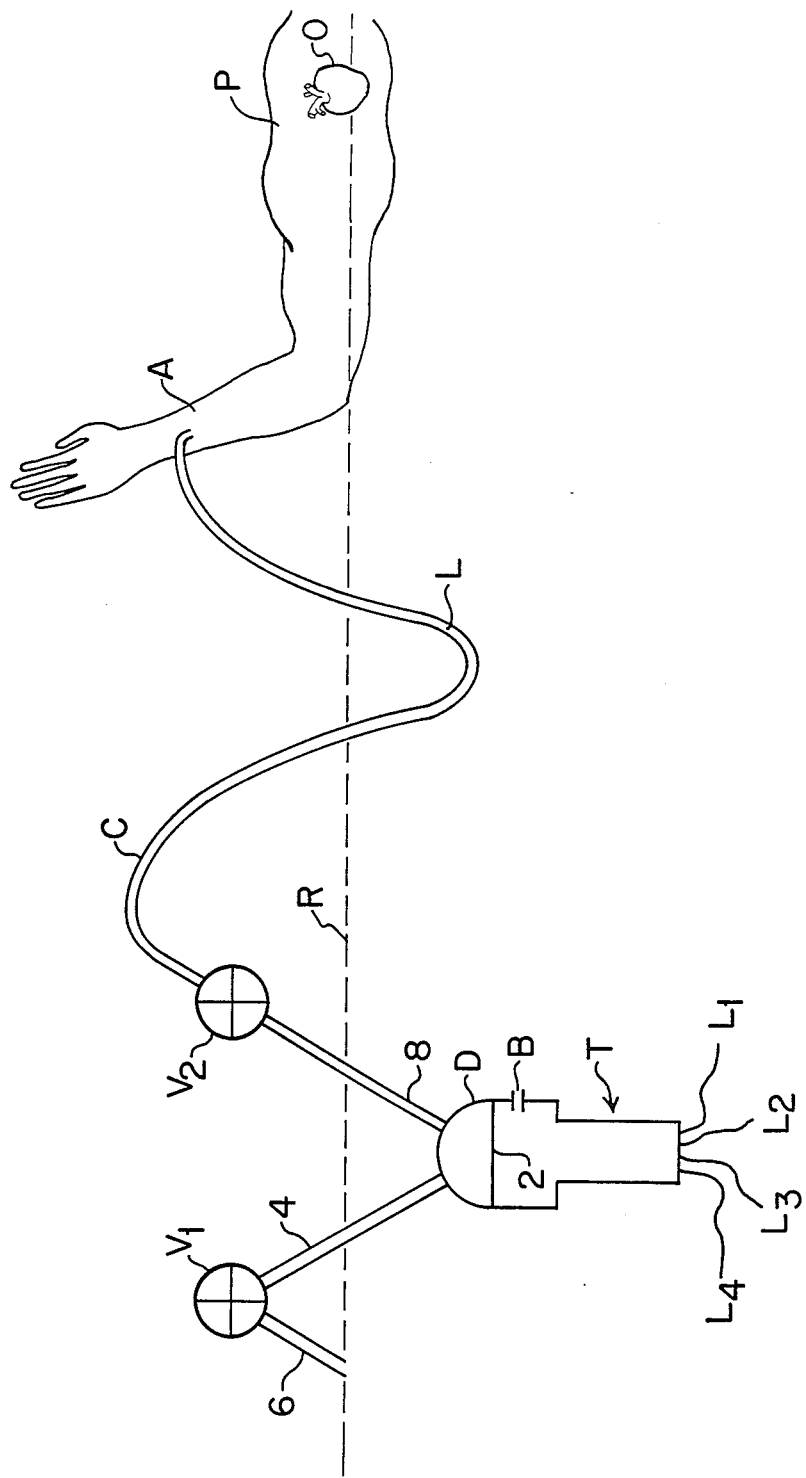
FIG. 1 illustrates apparatus of the prior art for indicating the blood pressure at a desired point in an organ of a patient.
Figure 2:
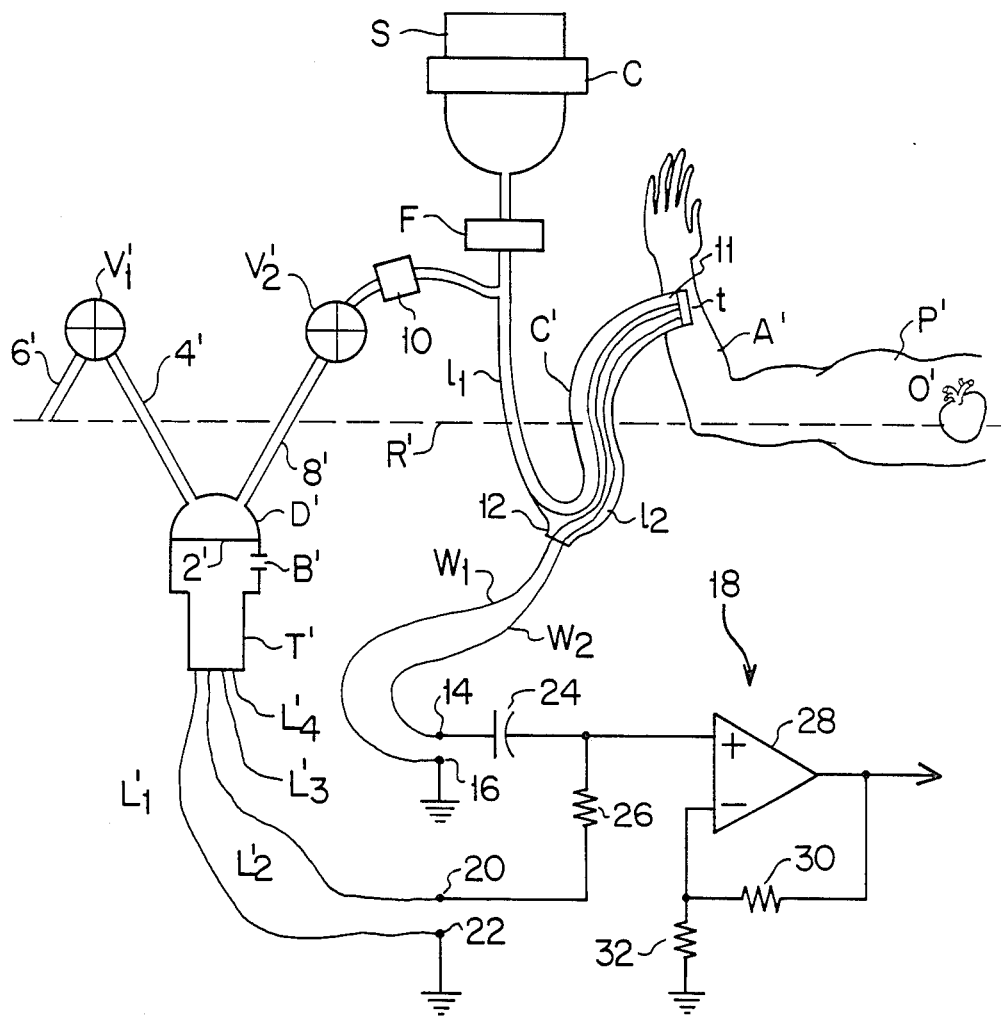
FIG. 2 illustrates one embodiment of apparatus constructed in accordance with this invention for indicating the blood pressure at a desired point in an organ of a patient.

In FIG. 2, the components corresponding in function to those of the prior art apparatus illustrated in FIG. 1 are indicated by the same characters primed.

The components associated with the external transducer T' are the same as in FIG. 1. In a preferred form, the means for coupling the dome D' to a lumen $l_1$ in the catheter C' includes a device 10 having a high hydraulic impedance as well as the tube 8' and the valve $V_2'$. The distal end of the catheter C' is inserted in a blood vessel in the arm A' of a patient and is provided with an internal transducer t. An opening 11 in the lumen $l_1$ is located close to the transducer t so that both are subjected to the same blood pressure. In order to keep blood from coagulating and blocking the opening 11, the other end of the lumen $l_1$ is coupled by a flush control device F to a source S of saline fluid that is kept under constant pressure by an inflatable cuff c. The flush control device F ordinarily permits a small continuous flow of solution through the lumen $l_1$ and out of the opening 11 so as to keep the opening 11 free from coagulated blood for a considerable length of time and, as known in the art, prevents the dissipation of the pressure wave into the saline fluid source S. Periodically, the flush control F may be operated to increase the flow substantially so as to flush out any blood remaining in the catheter C' after a blood sample is taken. The reason for not making the larger flow continuous is that it might injure the patient.

Leads $W_1$ and $W_2$ that run through another lumen $l_2$ in the catheter C' and out a plug 12 couple the internal transducer t to input terminals 14 and 16 of a means 18 for combining the signal from the internal transducer t with the signal on the leads $L_1'$ and $L_2'$ that is generated by the external transducer T. The leads $L_2'$ and $L_1'$ are respectively connected to terminals 20 and 22, and the terminals 16 and 22 are connected to ground. A capacitor 24 and a resistor 26 are connected in the order named between the terminal 14 and the terminal 20, and the junction between the capacitor 24 and the resistor 26 is connected to the non-inverting input of an operational amplifier 28. The output of the operational amplifier 28 is connected via a resistor 30 to its inverting input and a resistor 32 is connected between the inverting input and ground.

Figure 3:
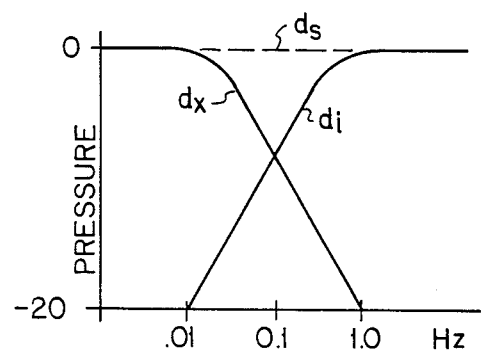
FIG. 3 is a graphical illustration of the de-emphasis of the signal components derived from each of the transducers.

Whereas the high frequency components provided by the internal transducer t correspond faithfully to the high frequency variations in blood pressure produced by the organ O, the low frequency components provided by the internal transducer t are drastically affected by changes in its elevation. For this reason, means (herein shown as being a high pass filter comprised of the resistor 26 and the capacitor 24) are provided for de-emphasizing the low frequencies in the signal provided by the internal transducer t so as to provide a first signal component to the non-inverting input of the amplifier 28. A satisfactory frequency response is illustrated by the graph $d_i$ in FIG. 3.

The low frequency components of the signal derived from the external transducer T' properly represent the mean pressure in the organ O' at the reference level R' and are unaffected by the raising or lowering of the patient's wrist in which the internal transducer t has been inserted; but for reasons previously given, any high frequency components derived from T' would be inaccurate. For this reason, means are provided for de-emphasizing high frequency components in a second signal component that would otherwise reach the non-inverting input of the amplifier 28 via the external transducer T'. The means may include one or all of the following: the lumen $l_1$ having a small internal diameter; the device 10 that provides a high hydraulic impedance; and the low pass filter comprised of the capacitor 24 and the resistor 26. A satisfactory frequency response resulting from the de-emphasis is, illustrated by a graph $d_x$ of FIG. 3. That the combined frequency response ds of the system is flat can be seen from the addition of the graphs dx and di.

Thus, the external transducer T' provides a component in the output signal of the amplifier 28 that corresponds to the mean blood pressure in the organ O'; and the internal transducer t provides a component in the output signal of the amplifier 28 that varies about the mean so that the signal at the output of the amplifier 28 accurately corresponds to the variations in blood pressure at the organ O'.

Other ways are known for keeping the opening 11 free from coagulation, e.g., coating it with an anticoagulant. If this method is used, the source S and flow control device F may be eliminated.

It is also possible to couple the signal from the internal transducer t to the signal combining network 18 by means other than the leads $W_1$ and $W_2$.

What is claimed is:

1. Apparatus for measuring the blood pressure of a patient, comprising
   a catheter,
   a first transducer mounted in an end portion of said catheter so as to produce at an output thereof means including a signal corresponding to blood pressure variation thereat,
   a lumen contained within said catheter,
   means defining an opening in said lumen at a point near said first transducer so that the blood pressure at said opening is the same as the blood pressure applied to said first transducer,
   means coupled to said first transducer for deriving a first signal component in which the low frequency components of the signal provided by said first transducer are de-emphasized,
   means for coupling a second transducer coupled to said lumen at a point remote from said opening for deriving a second signal component in which the high frequency components of the blood pressure variations at said opening are de-emphasized, and
   means for combining said signal components.

2. Apparatus as set forth in claim 1 in which the means for deriving the first signal component includes an electrical high pass filter coupled to the output of said first transducer.

3. Apparatus as set forth in claim 1 in which said means for deriving the second signal component includes means providing hydraulic impedance coupled between said opening and said second transducer for de-emphasizing the high frequency components in the second signal component.

4. Apparatus as set forth in claim 1 in which said means for deriving the second signal component includes a low pass electrical filter coupled to said second transducer for de-emphasizing the high frequency components in the second signal component.

5. Apparatus as set forth in claim 1 in which the de-emphasis of the low frequency components of said first signal and the de-emphasis of the high frequency components of said second signal are complementary.

6. Apparatus as set forth in claim 1 wherein a flush valve is coupled to said lumen.

7. Apparatus as set forth in claim 1 wherein said means for coupling said second transducer to said lumen includes a pressure dome.

8. Apparatus for measuring the blood pressure of a patient, comprising
- a first transducer for providing electrical signals corresponding to pressure variations applied to it,
- means whereby said first transducer may be coupled to a blood vessel of a patient so as to be subjected to the pressure of blood in said vessel,
- means coupled to said first transducer for deemphasizing the lower frequency components of the signals it provides,
- a second transducer for providing electrical signals corresponding to pressure variations applied to it,
- a conduit for coupling blood pressure variations that are applied to said first transducer to said second transducer,
- means for deemphasizing the high frequency components of signals provided by said second transducer, and
- means for combining the deemphasized signals derived from said first and second transducers.

* * * * *